United States Patent
Rautenberg (10) Patent No.: US 10,451,463 B2
(45) Date of Patent: Oct. 22, 2019

(54) DEVICE FOR DETERMINING PROPERTIES OF A MEDIUM COMPRISING A DAMPING ELEMENT AND/OR OPEN GUIDE ELEMENT

(71) Applicant: SENSACTION AG, Coburg (DE)

(72) Inventor: Jens Rautenberg, Coburg (DE)

(73) Assignee: SENSACTION AG, Coburg (DE)

( * ) Notice: Subject to any disclaimer, the term of this patent is extended or adjusted under 35 U.S.C. 154(b) by 0 days.

(21) Appl. No.: 16/072,127

(22) PCT Filed: Jan. 24, 2017

(86) PCT No.: PCT/EP2017/051429
§ 371 (c)(1),
(2) Date: Jul. 23, 2018

(87) PCT Pub. No.: WO2017/125612
PCT Pub. Date: Jul. 27, 2017

(65) Prior Publication Data
US 2019/0025101 A1    Jan. 24, 2019

(30) Foreign Application Priority Data
Jan. 24, 2016   (DE) .................. 10 2016 200 945

(51) Int. Cl.
*G01F 1/66* (2006.01)
*G01N 29/02* (2006.01)
(Continued)

(52) U.S. Cl.
CPC .......... *G01F 1/662* (2013.01); *G01N 29/024* (2013.01); *G01N 29/222* (2013.01);
(Continued)

(58) Field of Classification Search
CPC combination set(s) only.
See application file for complete search history.

(56) References Cited

U.S. PATENT DOCUMENTS

| 4,300,401 A | 11/1981 | Pedersen |
| 4,735,097 A | 4/1988 | Lynnworth |
| (Continued) | | |

FOREIGN PATENT DOCUMENTS

| DE | 195 03 714 A1 | 8/1996 |
| DE | 10 2009 048 646 A1 | 3/2011 |
| (Continued) | | |

OTHER PUBLICATIONS

Jackson, G.A., et al., "A three-path ultrasonic flowmeter for small-diameter pipelines," vol. 22, pp. 645-650 (1989).
(Continued)

*Primary Examiner* — Jewel V Dowtin
(74) *Attorney, Agent, or Firm* — Maschoff Brennan (57) ABSTRACT

It is provided an apparatus for determining at least one of physical, chemical and biological properties of a medium, comprising an acoustic waveguide, which has a conduction element with an inner side that faces the medium and an outer side that lies opposite this inner side. The inner side facing the medium is curved in concave fashion and the outer side is curved in convex fashion and the waveguide with the conduction element curved in that way is configured such that a second surface wave coupling-in at the concave inner side propagates along a propagation direction to the receiver. At least one damping element lies downstream of the receiver in the propagation direction of the second surface wave, said damping element being arranged and configured to prevent surface waves propagating counter to the propagation direction of the at least one second surface wave from reaching the receiver.

19 Claims, 3 Drawing Sheets

(51) Int. Cl.
*G01N 29/22* (2006.01)
*G01N 29/024* (2006.01)
*G01N 29/24* (2006.01)

(52) U.S. Cl.
CPC . *G01N 29/2462* (2013.01); *G01N 2291/0423* (2013.01); *G01N 2291/0428* (2013.01)

(56) References Cited

U.S. PATENT DOCUMENTS

| | | |
|---|---|---|
| 4,838,127 A | 6/1989 | Herremans et al. |
| 6,378,377 B2 | 4/2002 | Matuseski et al. |
| 6,513,365 B1 | 2/2003 | Bruetting et al. |
| 8,234,934 B2 | 8/2012 | Dietz et al. |
| 9,581,572 B2 | 2/2017 | Koenig et al. |
| 9,618,481 B2* | 4/2017 | Kruger ................. G01N 29/228 |
| 10,261,053 B2* | 4/2019 | Ten Grotenhuis ........................... G01N 29/0654 |
| 2015/0260561 A1 | 9/2015 | Twerdowski et al. |
| 2017/0276649 A1* | 9/2017 | Schmitz ............... G01N 29/043 |

FOREIGN PATENT DOCUMENTS

| | | |
|---|---|---|
| DE | 10 2011 119 673 A1 | 4/2013 |
| DE | 102012019217 A1 | 4/2014 |
| DE | 10 2014 106 706 A1 | 12/2014 |
| EP | 2 072 972 A1 | 6/2009 |
| EP | 2 343 548 A2 | 7/2011 |
| EP | 2 386 835 A1 | 11/2011 |
| WO | 9857163 A1 | 12/1998 |
| WO | 00/64737 | 11/2000 |
| WO | 2008/034878 A2 | 3/2008 |
| WO | 2015/096901 A1 | 7/2015 |

OTHER PUBLICATIONS

Jackson, G.A., et al., "A three-path ultrasonic flow meter with fluid velocity profile identification," vol. 22, pp. 635-642 (1991).
EP Office Action in application No. 17 705 026.7 dated Aug. 6, 2019.

* cited by examiner

DEVICE FOR DETERMINING PROPERTIES OF A MEDIUM COMPRISING A DAMPING ELEMENT AND/OR OPEN GUIDE ELEMENT

CROSS-REFERENCE TO A RELATED APPLICATION

This application is a National Phase Patent Application of International Patent Application Number PCT/EP2017/051429, filed on Jan. 24, 2017, which claims priority of German Patent Application 10 2016 200 945.1, filed on Jan. 24, 2016.

BACKGROUND

The present invention relates to an apparatus for determining physical and/or chemical and/or biological properties of a medium.

The medium whose physical, chemical and/or biological properties are to be determined by a generic method is preferably a liquid or a gas or a soft material, in particular a highly viscous, dough-like or pasty medium. The acoustic waves used to determine the properties are ultrasonic waves, for example, which are produced by an appropriate transmitter by way of a transmission signal.

In a known method for determining physical, chemical and/or biological properties of the medium, at least two acoustic waves, for example, are produced by a transmission signal, said acoustic waves propagating at least partly through the medium along identical or different propagation directions before they are each received at a receiver lying in the respective propagation direction. By way of example, in a flowing medium, acoustic waves are produced along a first propagation direction in the flow direction of the medium on the one hand and along a second propagation direction counter to the flow direction of the medium on the other hand. Then, a time-of-flight difference can be established from the reception signals generated at the respective receivers and this can be used to deduce the (mean) flow speed of the medium, for example. If, as an alternative or in addition thereto, times of flight and/or amplitudes and/or frequency changes of an acoustic wave from a transmitter to a receiver are still established with the aid of the reception signals, it is possible to draw further conclusions about physical, chemical and/or biological properties of the medium, such as the density, temperature or composition thereof, for example.

WO 2008/034878 A2 has disclosed an apparatus in which acoustic surface waves are produced, said surface waves coupling volume acoustic waves into the respective medium in a waveguide. By repeatedly output coupling surface waves at the sites at which the volume acoustic wave strikes a wall surrounding the medium, acoustic surface waves are received at a receiver in turn, the times of flight and time-of-flight differences of said surface waves being characteristic for the medium and the physical, chemical and/or biological properties thereof.

Consequently, in an apparatus described in WO 2008/034878 A2 and in the method implemented therewith, the processing of the reception signals, produced at the respective receivers, for a received acoustic wave—an acoustic surface wave in this case—plays a decisive role. Thus, establishing a time-of-flight difference or an absolute time of flight from the reception signals produced at the receivers is by no means trivial and, in certain circumstances, connected to significant computational outlay. Very different methods for signal processing are used, depending on the information to be extracted from the reception signals. By way of example, the use of modulated transmission signals to be able to deduce the properties of the medium in a more reliable fashion on the basis of the obtained reception signals is known.

Apart from that, there are ultrasonic methods for measuring the sound speeds in fluids, whether by a direct beam method or else by means of leaky Lamb wave based systems. The advantage of systems based on leaky Lamb waves lies in the great robustness in relation to dispersing particles or bubbles since, in comparison with the direct beam method, there is a significantly higher chance of components of the emitted sound packet also reaching the receiver. In addition to the sound speed, the temperature and, in particular, the substance density, too, are important measurement variables if a substance composition should be examined. There likewise are a number of different known measurement appliances for measuring the substance density. Within certain limits, the substance density likewise can be determined by Lamb wave sensors. However, a disadvantage of the available Lamb wave sensors lies in their comparatively large size, as result of which the access to many fields of applications is difficult. By way of example, long sensor embodiments, which can make the installation process more difficult, are required in pipes with a large nominal width on account of the beam paths. Moreover, an arrangement with opposing plates can make cleaning more difficult.

SUMMARY

It is therefore an object of the invention to provide an apparatus, improved in this respect, for determining physical, chemical and/or biological properties of a medium.

This object is achieved by an apparatus with features as described herein.

According to a first aspect of the invention, an apparatus for determining physical, chemical and/or biological properties of a medium is proposed, comprising an acoustic waveguide, which has a conduction element with an inner side that faces the medium and an outer side that lies opposite this inner side, at least one transmitter, by means of which at least one first surface wave is excitable at the conduction element, said at least one first surface wave propagating along the conduction element and, moreover, at least partly coupling into the medium as an acoustic wave, wherein the waveguide is embodied and configured such that the acoustic wave at least partly couples into the conduction element again as a second surface wave, at least one receiver, by means of which both first and second surface waves are receivable, and one electronic evaluation device that is at least coupled to the receiver, by means of which evaluation device physical, chemical and/or biological properties of the medium are determinable on the basis of received first and second surface waves.

Here, provision is further made for the inner side facing the medium to be curved in concave fashion and the outer side to be curved in convex fashion and the waveguide with the conduction element curved in that way to be configured such that a second surface wave coupling-in at the concave inner side propagates along a propagation direction to the receiver, and for provision to be made of at least one damping element that lies downstream of the receiver in the propagation direction of the second surface wave, said damping element being arranged and configured to prevent surface waves propagating counter to the propagation direction of the at least one second surface wave from reaching the receiver.

In one variant, the conduction element is adjoined by a portion of the waveguide as a damping element, which is curved and/or bent counter to the conduction element. In particular, this includes a configuration in which the transition between the conduction element and the portion serving as a damping element does not follow a continuous profile, in particular a circular path portion, but has a kink, for example. Further, a damping element is also understood to be a portion of the waveguide which, in the propagation direction of the second (and first) surface waves, is dimensioned downstream of the receiver in such a way that surface waves reflected at an end of this portion do not reach the receiver again or surface waves propagating in the propagation direction already do not reach the end. Thus, a type of attenuation path with a defined damping length is provided in a targeted manner downstream of the receiver.

Should the profile at least partly follow a circular path portion, provision is made according to one development for a bending radius r of the portion serving as a damping element to be less than a radius of curvature R of the conduction element. By way of example, R/r≥1.5 or R/r≥3.5 applies.

In one variant, an oppositely curved or oppositely bent portion also can be adjustable relative to the outer side of the conduction element. By way of example, the portion can have a flexible embodiment in order to be able to set the spatial position in relation to the outer side of the conduction element.

In an alternative or complementary manner, a (further) damping element can be formed by a separate element, which is formed or fastened to the conduction element or a portion of the waveguide adjoining the latter in the propagation direction of the second surface wave. By way of example, the separate element can comprise a potting compound, in particular potting compound in which the receiver is at least partly held.

In one embodiment variant, provision can be made for a potting compound to be situated between two opposite regions of a curved or bent portion that serves as a damping element. Here, the damping can be additionally increased by the potting compound, in particular if the potting compound connects the two opposite regions to one another. Consequently, the potting compound fills a channel or interstice, which is formed between the opposite regions, at least to such an extent that this channel or interstice is at least partly filled with potting compound and at least partly closed. In this way, the potting compound then stabilizes, i.e., stiffens, a bent portion, too, and can fix the latter relative to the outer side of the conduction element.

In principle, the waveguide can be part of a pipe or an open channel, in the interior of which the medium is situated. Alternatively, the waveguide is part of a sensor element that should be immersed into an interior filled with a medium for the purposes of determining the physical, chemical and/or biological properties of the medium. Hence, while the waveguide is embodied as part of a pipe guiding the medium, for example in the form of a pipe piece, and the medium can flow therethrough in the first aforementioned case, the waveguide is part of a sensor element to be immersed in the latter case, for example part of an immersion probe that is immersed into the medium such that the concave inner side of the conduction element is in contact with the medium.

In one embodiment variant, a radius of curvature R of the inner side of the conduction element is set depending on a frequency f in MHz of the at least one first surface wave to be excited, to be precise according to the formula $$R \geq \frac{30 \text{ mm} * \text{MHz}}{f}$$

It was found that particularly good measurement results can be obtained by the waveguide when predetermining the radius of curvature of the inner side according to the formula above and, in particular, that the evaluation of times of flight and time-of-flight differences of the received signal packets, on the basis of which the physical, chemical and/or biological properties of the medium are determined, is simplified.

In one embodiment variant, the waveguide has a holding portion,
  which serves as a handle for a user and/or
  which serves as a fastening element for a sensor integration and/or
  at which the damping element and/or a transmitter and/or receiver is arranged.

The handle of the waveguide, which optionally may also be formed at least in part by the conduction element, for example provides a defined gripping surface for the hand of the user in order to hold the waveguide in an interior filled with the medium. If the holding portion serves as a fastening element for sensor integration in an alternative or complementary manner, this provides an interface for fastening the waveguide to a sensor element and, for example, for connecting said waveguide to overarching sensor electronics and/or the electronic evaluation device. In an alternative or complementary manner, the holding portion can provide an attachment surface for an (additional) damping element and/or an (additional) transmitter and/or an (additional) receiver.

By way of example, the holding portion at the waveguide can have an embodiment with a straight-lined profile and adjoin the curved conduction element. In one embodiment variant, the conduction element, in a cross-sectional view, is provided at one end with a curved and/or bent portion that serves as a damping element while the other end of the conduction element adjoins the holding portion that extends in a straight line.

In one embodiment variant, the conduction element is curved and the transmitter and the receiver are aligned to one another in such a way that a propagation direction of the acoustic waves in the medium extends at an angle ≥30° with respect to the central axis about which the inner side, which is curved in concave fashion, of the conduction element extends. Consequently, the curvature of the conduction element and the positioning of the transmitters and the receivers relative to one another on the conduction element are matched to one another here—for example, on the basis of trial structures—and are selected in such a way that the desired angle range for the propagation direction of the acoustic wave relative to the central axis is always provided when the first surface waves are excited. It was found that advantages during the measurement and evaluation can be obtainable in certain embodiment variants under these stipulations.

In principle, the waveguide can have at least two transmitter-receiver pairs in order to excite surface waves in different propagation directions and hence possibly increase the measurement accuracy.

In an alternative or complementary manner, a transmitter and a receiver can be provided by transmitter-receiver unit, which is selectively operable as a transmitter or as a receiver. In particular, the transmitter and/or the receiver also can be formed by a transducer, in particular an interdigital transducer or a wedge transducer.

In principle, the transmitter can be configured and provided to excite Lamb waves or waves in the transition region of Lamb and Rayleigh waves.

According to a second aspect of the invention, an apparatus for determining physical, chemical and/or biological properties of a medium is proposed, in which
the conduction element is open on one side and the inner side facing the medium is curved in concave fashion and the outer side is curved in convex fashion and the waveguide with a conduction element curved on one side in that way is configured such that a second surface wave coupling-in at the concave inner side propagates along a propagation direction to the receiver, and
the waveguide is part of a sensor element that should be immersed into an interior filled with a medium for the purposes of determining the physical, chemical and/or biological properties of the medium.

Consequently, no conduction element completely surrounding the medium on the circumferential side and no opposite, further conduction element are provided in a (measurement) apparatus according to the second aspect of the invention. Consequently, an opposite plate as a further conduction element, as provided in the previously conventional measurement apparatuses operating on the basis of surface waves, is missing in particular. By contrast, an open structure of the waveguide is provided according to the second aspect of the invention, which is readily combinable with the first aspect of the invention, and so the waveguide with the conduction element has a C-shaped or U-shaped cross section, for example.

Here, in particular, the proposed method is implementable by means of the proposed apparatus such that advantages and features of embodiment variants of the method, explained both above and below, also apply to embodiment variants of the apparatus, and vice versa.

BRIEF DESCRIPTION OF THE DRAWINGS

The attached figures elucidate possible exemplary embodiments of the proposed solution in an exemplary manner.

DETAILED DESCRIPTION

Figure 1:
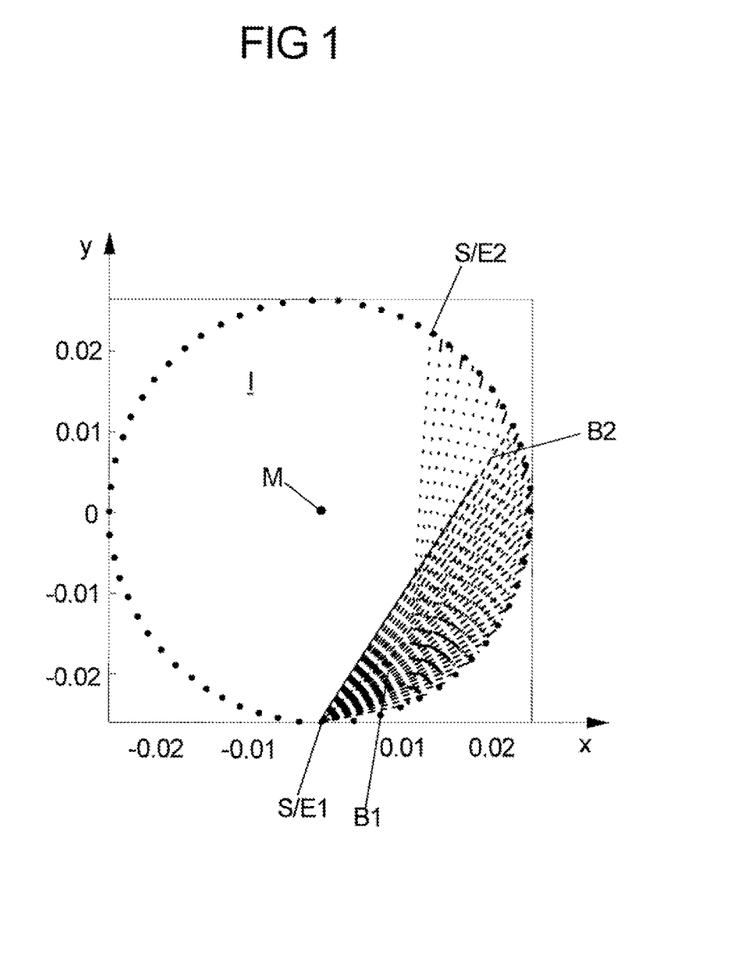
FIG. 1 schematically shows a cross-sectional view of a (measurement) apparatus according to the invention.

Here, FIG. 1 schematically shows an embodiment variant of a (measurement) apparatus according to the invention in a cross-sectional view. Further, FIGS. 2A to 2D show different variants of a (measurement) apparatus V according to the invention. The measurement apparatuses V of FIGS. 1 and 2A-2D each have a conduction element 11, which is embodied here as a bent plate, a single pipe segment or an open channel, and on which first surface waves OW1 are excitable by means of the transmitter-receiver units S/E1, S/E2 that are operated as transmitters. The waveguide of the illustrated management apparatuses V in each case is part of a sensor element that is immersed into an interior I filled with a medium F for the purposes of determining the physical, chemical and/or biological properties of the medium F.

The conduction element 11 has an inner side 110, which, when the measurement apparatus V is used as intended, faces the medium F whose physical, chemical and/or biological properties are to be determined. An outer side 111 of the conduction element 11, lying opposite the inner side 110, is curved in convex fashion. A waveguide of the measurement apparatus V defined with the conduction element 11 is configured with the conduction element 11 curved thus such that a second surface wave OW2, which is produced by means of a transmitter S/E1, S/E2 and coupled-in at the concave inner side 110, propagates along the propagation direction to a receiver S/E2, S/E1 arranged at the conduction element 11. A damping element 10, 12, 22a or 22b lying downstream of the receiver S/E1, S/E2 in the propagation direction of the second surface wave OW2. The respective damping element 10, 12, 22a, 22b is arranged and configured to prevent surface waves propagating counter to the propagation direction of the at least one second surface wave OW2 from reaching the receiver S/E1, S/E2.

By way of example, potting compounds 22a, 22b and portions 10 and 12 that are bent counter to the curvature of the conduction element 11, for example, serve as damping elements. What is achieved here in each case by way of the damping elements is that a transmitter-receiver unit S/E2, S/E1 that is operated as a receiver is only reached by first and second surface waves OW1 and OW2 that have propagated to the receiver or this transmitter-receiver unit S/E2, S/E1 along a (main) propagation direction at the conduction element 11. Surface waves propagating counter thereto, which arise by reflections at an open end of the waveguide, for example, are not received as a result thereof.

In the proposed variants of FIGS. 1 and 2A-2D, a bent plate (circle segment of a fluid-guiding pipe), for example, is proposed as a conduction element 11, which contacts the medium to be characterized, in this case a fluid, at one side. The Lamb wave is excited on the plate by a transmitter-receiver unit S/E1, S/E2 in the form of a piezo-ceramic (interdigital transducer or wedge transducer). On the waveguiding bent plate, it reaches a second piezo-ceramic, which acts as a receiver S/E2, S/E1. Additionally, a part of the wave reaches the same plate through the adjacent fluid with a time offset as a leaky wave volume, where it is coupled-in again (on account of the reciprocity in the case of an unchanging bending radius) and where it runs in the direction of the receiver S/E2, S/E1. Consequently, it is possible to detect two signal packets at the receiver S/E2, S/E1, the time of flight and time-of-flight difference thereof being used predominantly for determining the sound speed, the amplitude ratio thereof being used to calculate the substance density and the time of flight of the first wave packet thereof being used to measure the temperature. To this end, an electronic evaluation device AS is provided, the latter being coupled to the transmitter and receiver units S/E2 and S/E1 (only illustrated in FIG. 2A). Physical, chemical and/or biological properties of the medium F are determinable by means of this electronic evaluation device AS—in a manner known per se in terms of principles (see, for example, WO 2008/034878 A2)—on the basis of received first and second surface waves OW1, OW2.

Consequently, two embodiments, in particular, are conceivable as a result thereof:
1. Transmitter and receiver are arranged transversely, or at an angle >0°, to the axis of a pipe or a pipe segment with the main propagation direction of the sound. The waves mainly run in the circumferential direction; components in the direction of the pipe axis are allowed. More compact in-line variants can be realized in this manner.
2. Transmitter and receiver are installed in an open pipe segment. In this way, it is possible to realize sensor elements, for example in the form of immersion probes, that are more robust and easier to clean.

FIG. 1 shows, in an exemplary fashion, the beam paths in the fluid at an angle of the sound path of 90° with respect to the axis of the imagined pipe for a typical measurement range of the sound speed (DN50; mid frequency of the sound is at 1.5 MHz; region B1: first relevant sound components; region B2: last relevant sound components).

The origin in the region B1 of a fan opening up in a manner corresponding to FIG. 1 denotes a position of the transmitter whereas the uppermost point in the region B2 specifies the position of the receiver. In the case of an apparatus V configured as an immersion probe, the suggestion now is that the sound components immediately behind the receiver (i.e., behind the transmitter-receiver unit S/E2 operated as a receiver) are deflected to the back by a plate that is tightly bent to the outside (radius r greater than, for example, 1.5*plate thickness d) so that a second signal packet 2 can reach the receiver in unimpeded fashion. Transmitter and receiver S/E1, S/E2 can also be operated in reverse; in that case, they have plate ends bent on both sides. The position of the receiver S/E2 should be adapted to the greatest sound speed to be measured for the purposes of an improved sensitivity. Here, the following rule applies: as the sound speed to be measured increases, so does the size of the pipe segment (in the form of the bent conduction element 11) to be used, which is denoted by the two described points.

The illustrated variants of the measurement apparatus V according to the invention in this case respectively serve to measure the sound speed, density and temperature and, derived therefrom, the composition in terms of substances of the fluid F (as a realization of any medium) by means of guided acoustic Lamb waves, consisting of a pipe segment with a one-sided fluid contact and at least two piezo-electric transmitter-receiver units S/E1, S/E2. Here, the following features can be implemented individually or cumulatively:

A bending radius R of the wave-guiding plate or conduction element 10 is at least 30 mm*MHz/frequency f [MHz]. Thus, this is correspondingly at least 20 mm at 1.5 MHz.

The transmission and reception elements are aligned in relation to one another over a trajectory along the pipe segment in such a way that the main propagation direction of the acoustic wave is greater than 38°, to at most perpendicular, to an (imagined) pipe axis.

The piezo-ceramic transmitters/receivers (S/E1, S/E2) are designed as interdigital transducers or wedge transducers for exciting Lamb waves or Rayleigh waves.

The pipe segment or the conduction element 11 is a constituent part of a pipe that is closed in the circumferential direction.

The ends of the pipe segment or the portions 10 and 12 of the waveguide adjoining the conduction element 10 are bent to the back by tight bends (radius r greater than 1.5*plate thickness d) Here, the ends 10 and 12 of these bent plate segments can each have half the length of the circular arc (variants in FIGS. 2B and 2C) and/or the plate ends can be provided with damping potting compounds (variants in FIGS. 2A to 2D). The precise end position of the bent (plate) end 10 or 12 is not relevant here.

Figure 2A:
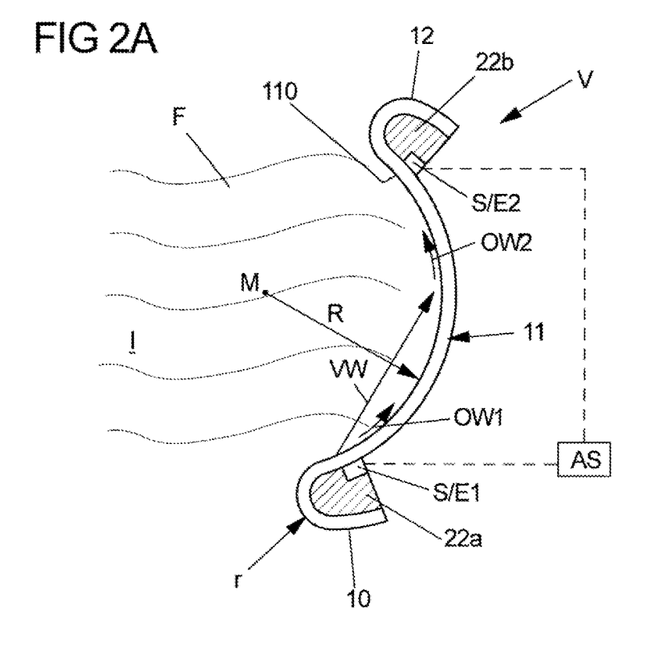
FIGS. 2A-2D each show a cross-sectional view of variants of the (measurement) apparatus according to the invention.

Here, FIG. 2A shows an embodiment variant with relatively short bent conduction element ends 10, 12, which each define a damping element and have a potting compound 22a, 22b. Thus, a channel or interstice that is partly or completely filled with a potting compound is formed in an end of the conduction element 11 that is bent—to the outside in relation to the inner side 110. Here, the channel has a U-shaped cross section, for example, and also receives the transmitter-receiver unit S/E1 or S/E2 that is arranged in the region of the respective conduction element end. In this way, the respective transmitter-receiver unit S/E1 or S/E2 that is arranged at the outer side 111 can also be partly or completely embedded in the potting compound of the associated damping element 22a or 22b.

Figure 2B:
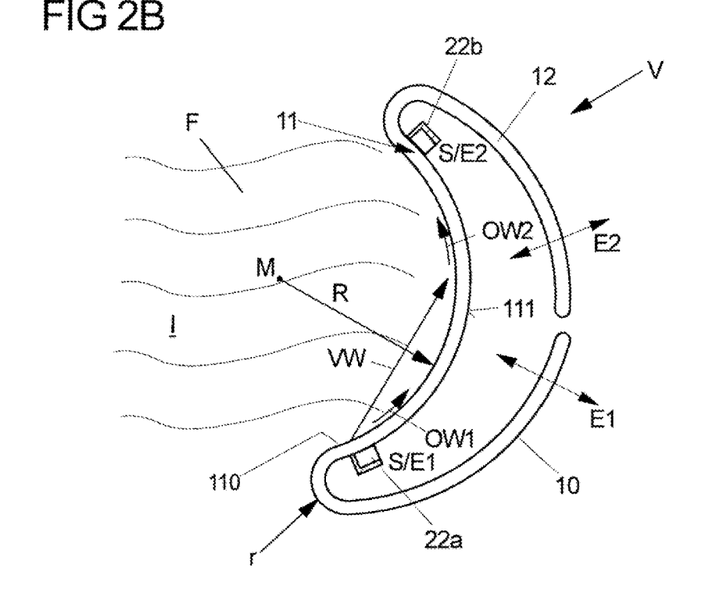

FIG. 2B shows a variant with long bent plate ends or conduction element ends 10, 12, which once again define damping elements. Casting the plate at this end is optional in this case; nevertheless, each transmitter-receiver unit S/E1 and S/E2 is partly embedded in a potting compound 22A, 22b at the outer side 111. However, in comparison with the variant of FIG. 2A, the potting compound 22a, 22b is only applied locally and, in particular, it does not fill the channel respectively defined by the ends 10 and 12 that are bent to the outside and therefore it also does not connect to opposite regions at the curved, bent conduction element end 10 or 12.

The ends bent to the outer side 111 with a comparatively long embodiment, i.e., in each case with a length in the region of at least ⅓ or ½ of the distance between the transmitter and receiver units S/E1 and S/E2, already ensure sufficient damping. Here, further, a bending radius r of the bent ends is significantly smaller than the radius of curvature R of the inner side 10 for the purposes of promoting the damping.

By virtue of the bent ends 10 and 12 pointing to one another, which define the damping elements, not being provided with a potting compound 22a or 22b in each case in the present case, said ends in each case provide an elasticity portion E1 or E2. The respective end 10 or 12 is flexible in the elasticity portions E1 or E2 so as to be able to set its spatial position in relation to the outer side 111 of the conduction element 11. In this way, it is still possible to displace the respective conduction element end 10 or 12 relative to the outer side 111 and hence bend the conduction element more open or bend it more shut. As a result of this, it is possible to modify the bending radius r, in particular since conduction element end 10 or 12 is not stabilized or fixed by a potting compound.

Figure 2C:
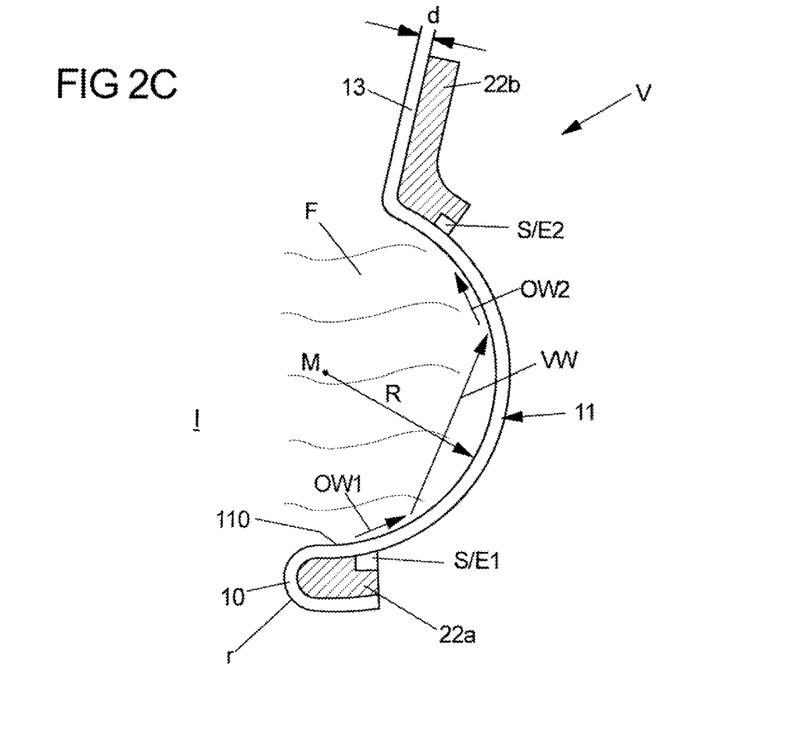
Figure 2D:
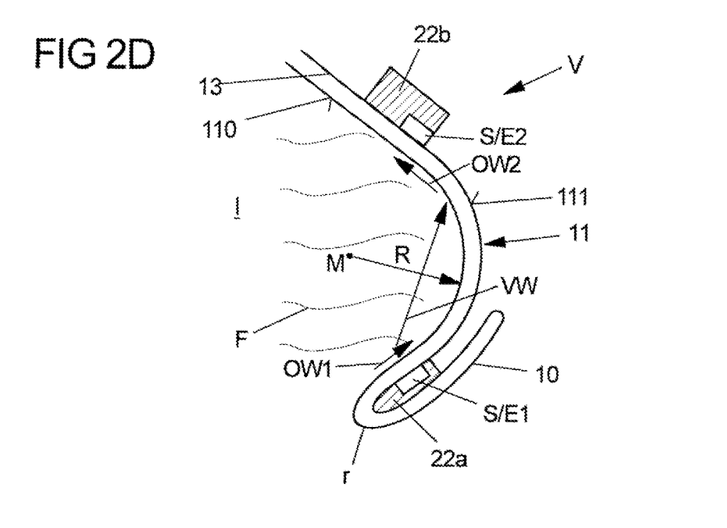

FIGS. 2C and 2D each show a variant with only a short end plate and/or conduction element end 10 of different lengths (short in FIG. 2C; long in FIG. 2D), combined with a long plate and or conduction element end. Once again, a potting compound 22a is provided at the conduction element end 10 bent toward the outer side 111, said potting compound completely (FIG. 2C) or partly (FIG. 2D) filling the channel or interstice formed and affixing the respective bent conduction element 10, with the transmitter-receiver unit S/E1 operated as a transmitter being partly (FIG. 2C) or completely (FIG. 2D) embedded in said potting compound.

The respective long end lying in the propagation direction of the surface waves OW1, OW2 further forms a holding portion 13, for example as part of a grip or a housing. Here, the potting compound 22b can be applied in a large area on the holding portion 13 (FIG. 2c) and/or it can once again only be applied locally in order to arrange a transmitter-receiver unit S/E2 herein (such that the transmitter-receiver unit S/E2 is at least partly held in the potting compound 22b; see FIG. 2D).

The transmitters-receiving unit S/E2 operated as a receiver can be arranged at the convex outer side 111, according to the embodiment variants illustrated in FIGS. 2C and 2D, or it can be arranged at the longer plate end, which possibly extends in a straight line and which forms the holding portion 13.

LIST OF REFERENCE SIGNS 1 1st Signal packet
10 Conduction element end/damping element
11 Pipe segment (bent conduction element)
110 Inner side
111 Outer side
12 Conduction element end/damping element
13 Holding portion
2 2nd Signal packet
22a, 22b Potting compound (damping element)
AS Evaluation device
B1, B2 Region
d Wall/plate thickness
E1, E2 Elasticity portion
F Fluid (medium)
I Interior
M Central axis/center point
OW1, OW2 Surface wave
R, r Radius
S/E1, S/E2 Transmitter-receiver unit
V (Measurement) apparatus
VW Volume acoustic wave

The invention claimed is:

1. An apparatus for determining at least one of physical, chemical and biological properties of a medium, comprising:
an acoustic waveguide, which has a conduction element with an inner side that faces the medium and an outer side that lies opposite this inner side,
at least one transmitter, by means of which at least one first surface wave is excitable at the conduction element, said at least one first surface wave propagating along the conduction element and, moreover, at least partly coupling into the medium as an acoustic wave, wherein the waveguide is embodied and configured such that the acoustic wave at least partly couples into the conduction element again as a second surface wave,
at least one receiver, by means of which both first and second surface waves are receivable, and
one electronic evaluation device that is coupled at least to the receiver, by means of which evaluation device at least one of physical, chemical and biological properties of the medium are determinable on the basis of received first and second surface waves, wherein:
the inner side facing the medium is curved in concave fashion and the outer side is curved in convex fashion and the waveguide with the conduction element curved in that way is configured such that a second surface wave coupling-in at the concave inner side propagates along a propagation direction to the receiver, and
provision is made of at least one damping element that lies downstream of the receiver in the propagation direction of the second surface wave, said damping element being arranged and configured to prevent surface waves propagating counter to the propagation direction of the at least one second surface wave from reaching the receiver.

2. The apparatus as claimed in claim 1, wherein the conduction element is adjoined by a portion of the waveguide as a damping element, which is curved and/or bent counter to the conduction element.

3. The apparatus as claimed in claim 2, wherein a bending radius r of the portion serving as a damping element is less than a radius of curvature R of the conduction element.

4. The apparatus as claimed in claim 3, wherein R/r≥1.5, in particular R/r≥3.5, applies to the ratio between radius of curvature R and bending radius r.

5. The apparatus as claimed in claim 2, wherein an oppositely curved or oppositely bent portion is adjustable, in particular flexible, relative to the outer side of the conduction element in order to be able to set the spatial position relative to the outer side of the conduction element.

6. The apparatus as claimed in claim 1, wherein the damping element is formed by a separate element, which is formed or fastened to the conduction element or a portion of the waveguide adjoining the latter in the propagation direction of the second surface wave.

7. The apparatus as claimed in claim 6, wherein the separate element comprises a potting compound.

8. The apparatus as claimed in claim 7, wherein the receiver is at least partly held in a potting compound.

9. The apparatus as claimed in claim 2, wherein the separate element comprises a potting compound which is situated between two opposite regions on the curved or bent portion.

10. The apparatus as claimed in claim 9, wherein the potting compound connects the two opposite regions to one another.

11. The apparatus as claimed in claim 1, wherein the waveguide is at least one of the following
part of a pipe or open channel, in the interior of which the medium is situated, and
part of a sensor element that should be immersed into an interior filled with a medium for the purposes of determining the at least one of physical, chemical and biological properties of the medium.

12. The apparatus as claimed in claim 1, wherein a radius of curvature R of the inner side of the conduction element is set depending on a frequency f in MHz of the at least one first surface wave to be excited, to be precise according to the formula $$R \geq \frac{30 \text{ mm} * \text{MHz}}{f}.$$

13. The apparatus as claimed in claim 1, wherein the waveguide has a holding portion:
which serves as a handle for a user and/or
which serves as a fastening element for a sensor integration and/or
at which the damping element and/or a transmitter and/or receiver is arranged.

14. The apparatus as claimed in claim 1, wherein the conduction element is curved and the transmitter and the receiver are aligned to one another in such a way that a propagation direction of the acoustic waves in the medium extends at an angle ≥30° with respect to a central axis about which the inner side, which is curved in concave fashion, of the conduction element extends.

15. The apparatus as claimed in claim 1, wherein the waveguide has at least two transmitter-receiver pairs.

16. The apparatus as claimed in claim 1, wherein a transmitter and a receiver are provided by a transmitter-receiver unit, which is selectively operable as a transmitter or as a receiver.

17. The apparatus as claimed in claim 1, wherein the transmitter and/or the receiver are formed by a transducer, in particular an interdigital transducer or a wedge transducer.

18. The apparatus as claimed in claim 1, wherein the transmitter is configured and provided to excite Lamb waves or waves in the transition region between Lamb and Rayleigh waves.

19. An apparatus for determining at least one of physical, chemical and biological properties of a medium, comprising
- an acoustic waveguide, which has a conduction element with an inner side that faces the medium and an outer side that lies opposite this inner side,
- at least one transmitter, by means of which at least one first surface wave is excitable at the conduction element, said at least one first surface wave propagating along the conduction element and, moreover, at least partly coupling into the medium as an acoustic wave, wherein the waveguide is embodied and configured such that the acoustic wave at least partly couples into the conduction element again as a second surface wave,
- at least one receiver, by means of which both first and second surface waves are receivable, and
- one electronic evaluation device that is coupled at least to the receiver, by means of which evaluation device at least one of physical, chemical and biological properties of the medium are determinable on the basis of received first and second surface waves, wherein:
  - the inner side facing the medium is curved in concave fashion and the outer side is curved in convex fashion and the waveguide with a conduction element curved on one side in that way is configured such that a second surface wave coupling-in at the concave inner side propagates along a propagation direction to the receiver, and
  - the waveguide is part of a sensor element that should be immersed into an interior filled with a medium for the purposes of determining at least one of the physical, chemical and biological properties of the medium.

* * * * *